(12) United States Patent
Ting et al.

(10) Patent No.: US 10,953,246 B2
(45) Date of Patent: Mar. 23, 2021

(54) PIEZOELECTRIC SYSTEM FOR ULTRASONIC THERMOTHERAPY AND ELECTROTHERAPY

(71) Applicant: Chung-Yuan Christian University, Tao Yuan County (TW)

(72) Inventors: Yung Ting, Tao Yuan County (TW); Sheuan-Perng Lin, Tao Yuan County (TW); Chih-Hsuan Yu, Tao Yuan County (TW)

(73) Assignee: Chung-Yuan Christian University, Chung Li (TW)

( * ) Notice: Subject to any disclaimer, the term of this patent is extended or adjusted under 35 U.S.C. 154(b) by 574 days.

(21) Appl. No.: 15/817,952

(22) Filed: Nov. 20, 2017

(65) Prior Publication Data

US 2019/0060676 A1 Feb. 28, 2019

(30) Foreign Application Priority Data

Aug. 30, 2017 (TW) ................. 106129547

(51) Int. Cl.
  *A61N 7/02* (2006.01)
  *B06B 1/02* (2006.01)
  (Continued)

(52) U.S. Cl.
  CPC ............. *A61N 7/02* (2013.01); *A61H 39/002* (2013.01); *A61H 39/007* (2013.01); *A61H 39/06* (2013.01); *A61H 39/08* (2013.01); *A61N 1/025* (2013.01); *A61N 1/0456* (2013.01); *A61N 7/00* (2013.01); *B06B 1/023* (2013.01); *B06B 1/0618* (2013.01); *A61H 2201/0153* (2013.01); *A61H 2201/10* (2013.01); *A61H 2201/1207* (2013.01); *A61H 2201/169* (2013.01); *A61H 2201/1654* (2013.01); *A61H 2201/50* (2013.01);
  (Continued)

(58) Field of Classification Search
  None
  See application file for complete search history.

(56) References Cited

U.S. PATENT DOCUMENTS 8,836,202 B2 9/2014 Ting et al.
2010/0331869 A1* 12/2010 Voegele ................ B06B 1/0607
606/169

(Continued)

*Primary Examiner* — Katherine L Fernandez
(74) *Attorney, Agent, or Firm* — Muncy, Geissler, Olds & Lowe, P.C.

(57) ABSTRACT

A piezoelectric system for ultrasonic thermotherapy and electrotherapy comprises a first piezoelectric element, a proof mass, a second piezoelectric element and an output unit. The proof mass is disposed between the first piezoelectric element and the second piezoelectric element. The first piezoelectric element is powered by a power source to generate oscillation, which is transferred by the proof mass to the second piezoelectric element so as to cause the second piezoelectric element to move and generate power. The output unit comprises a connecting surface and a tip surface. The output unit is electronically connected with the second piezoelectric element, wherein the connecting surface is connected with the first piezoelectric element and the tip surface is formed in a tapered shape. The oscillation from the first piezoelectric element and the power generated by the second piezoelectric element are output through the tip surface.

8 Claims, 11 Drawing Sheets

(51) Int. Cl.
  *B06B 1/06* (2006.01)
  *A61N 1/02* (2006.01)
  *A61H 39/00* (2006.01)
  *A61N 1/04* (2006.01)
  *A61H 39/08* (2006.01)
  *A61N 7/00* (2006.01)
  *A61H 39/06* (2006.01)
  *A61N 1/36* (2006.01)

(52) U.S. Cl.
  CPC .... *A61H 2201/5005* (2013.01); *A61N 1/0472* (2013.01); *A61N 1/36014* (2013.01); *A61N 2007/0026* (2013.01); *A61N 2007/0078* (2013.01); *B06B 2201/76* (2013.01)

(56) References Cited

U.S. PATENT DOCUMENTS

| | | | | |
|---|---|---|---|---|
| 2013/0300258 | A1* | 11/2013 | Ting | H02N 2/186 310/339 |
| 2015/0088154 | A1* | 3/2015 | Vaitekunas | B06B 1/0253 606/128 |
| 2015/0188023 | A1* | 7/2015 | Pond | H01L 41/09 433/86 |

* cited by examiner

PIEZOELECTRIC SYSTEM FOR ULTRASONIC THERMOTHERAPY AND ELECTROTHERAPY

BACKGROUND OF THE INVENTION

1. Field of the Invention

The present invention relates to a piezoelectric system for ultrasonic thermotherapy and electrotherapy, and more particularly, to a piezoelectric system for ultrasonic thermotherapy and electrotherapy which can simultaneously provide the voltage required for physical electrotherapy and oscillation for ultrasonic therapy.

2. Description of the Related Art

Generally, piezoelectric components are used to convert mechanical energy into electrical energy, or to convert electrical energy into mechanical energy; however, since piezoelectric components can use a voltage to generate oscillation and can also use the oscillation (resulting in deformation) to generate electricity, it is possible to use two piezoelectric elements in a system, where one piezoelectric element is used as the source of the oscillation and the other as the power source, thereby providing various applications by using the oscillating characteristics of the piezoelectric elements. U.S. Pat. No. 8,836,202 discloses a composite piezoelectric system in which two piezoelectric elements are used in a system with one acting as an oscillation source and the other as a power source, such that the composite piezoelectric system uses the oscillating characteristics of piezoelectric elements to generate electricity. However, this composite piezoelectric system is not designed for ultrasonic thermotherapy and electrotherapy, so this type of piezoelectric system is still worthy of further research and development for different applications.

Traditionally, in performing electro-acupuncture stimulation, the user will wear a bracelet or patch, or alternatively the user will hold a metal conductor acting as the negative electrode or sit on a chair containing the negative electrode, to help form an electrical stimulation circuit. Whether it is bracelet, patch or chair containing the negative electrode, the types of electrotherapy components are various and their operations are complicated; furthermore, such electrotherapy components cannot provide ultrasonic thermotherapy at the same time. Therefore, the convenience and functionality of the electrotherapy components can be further improved.

SUMMARY OF THE INVENTION

It is an object of the present invention to provide a piezoelectric system for ultrasonic thermotherapy and electrotherapy which can simultaneously provide the voltage required for physical electrotherapy and oscillation for ultrasonic therapy.

In order to achieve the above object, the present invention discloses a piezoelectric system for ultrasonic thermotherapy and electrotherapy, which comprises a first piezoelectric element, a second piezoelectric element, a proof mass, and an output unit. The first piezoelectric element is disposed between the output unit and the proof mass. The proof mass is disposed between the first piezoelectric element and the second piezoelectric element. The first piezoelectric element is powered by a power source to generate an oscillation, which is transferred by the proof mass to the second piezoelectric element so as to cause the second piezoelectric element to move and generate power. The output unit comprises a connecting surface and a tip surface. The output unit is electronically connected with the second piezoelectric element, wherein the connecting surface is connected with the first piezoelectric element. The oscillation from the first piezoelectric element and the power generated by the second piezoelectric element are output through the tip surface.

The piezoelectric system for ultrasonic thermotherapy and electrotherapy of the present invention comprises two piezoelectric elements, wherein the first piezoelectric element is used as an actuator and is driven by the power source to generate a high amplitude oscillation, which partly is transferred by the proof mass to the second piezoelectric element; the second piezoelectric element receives part of the oscillation energy from the actuator and generates power for medical applications based on the piezoelectric effect, thereby providing the voltage required for physical electrotherapy and the oscillation for ultrasonic therapy at the output unit at the same time.

DETAILED DESCRIPTION OF THE PREFERRED EMBODIMENT

To clarify the technical content of the present invention, the preferred embodiments of the present invention are described as follows. Please refer to FIG. 1A, FIG. 1B, and FIG. 2 for a schematic diagram, system block diagram, and operation diagram of the first embodiment of the piezoelectric system for ultrasonic thermotherapy and electrotherapy of the present invention.

Figure 1A:
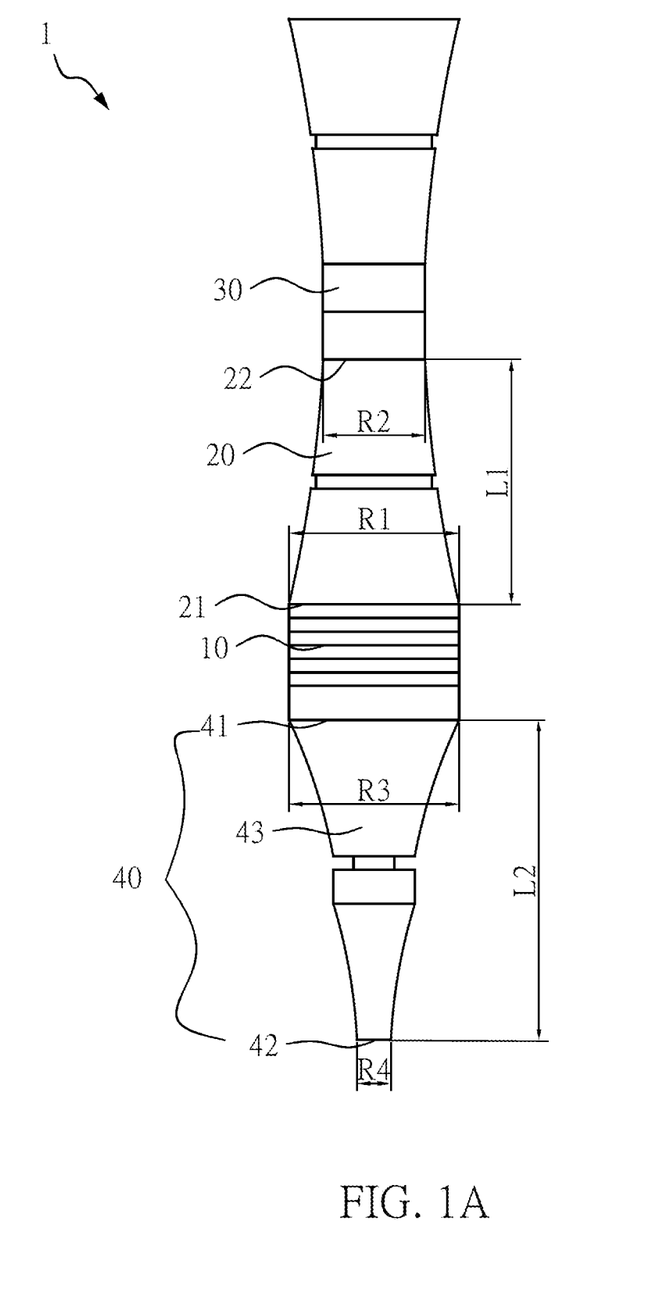
FIG. 1A illustrates a schematic diagram of a first embodiment of the piezoelectric system for ultrasonic thermotherapy and electrotherapy of the present invention.
Figure 1B:
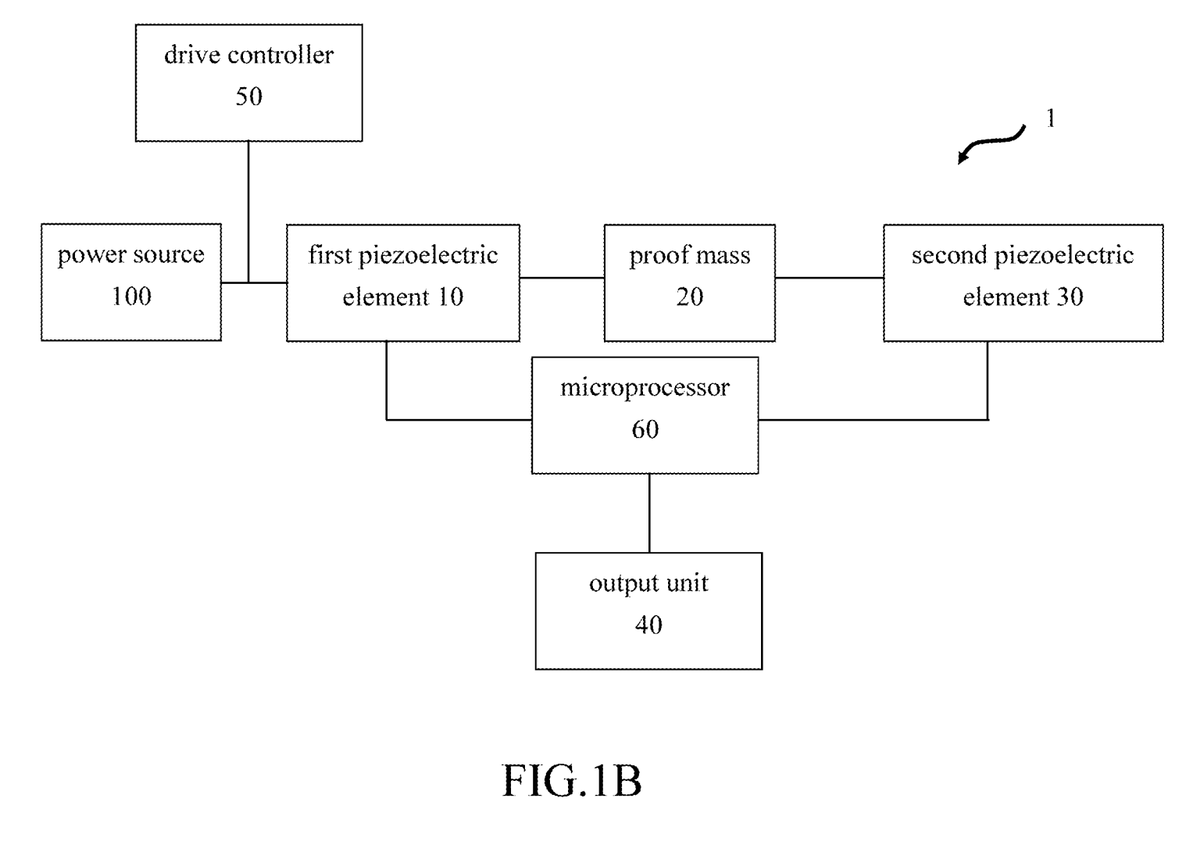
FIG. 1B illustrates a block diagram of the piezoelectric system for ultrasonic thermotherapy and electrotherapy of the present invention.
Figure 2:
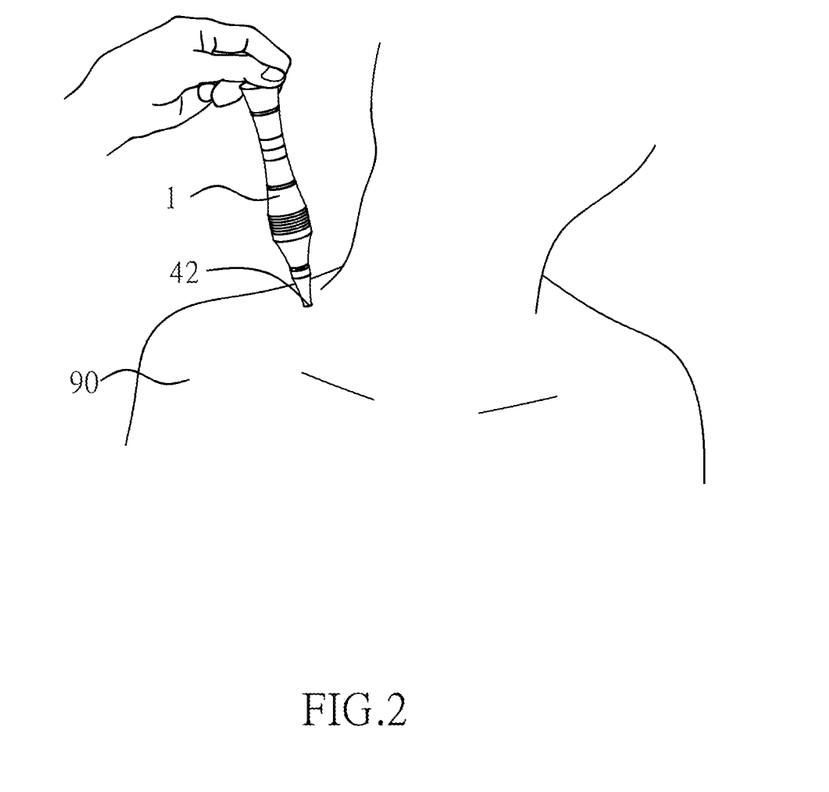
FIG. 2 illustrates an operation diagram of the first embodiment of the piezoelectric system for ultrasonic thermotherapy and electrotherapy of the present invention.

As shown in FIG. 1A and FIG. 1B, in the present embodiment, a piezoelectric system for ultrasonic thermotherapy and electrotherapy 1 comprises a first piezoelectric element 10, a proof mass 20, a second piezoelectric element 30, an output unit 40, a drive controller 50, and a microprocessor 60. The first piezoelectric element 10 is disposed between the output unit 40 and the proof mass 20, and the proof mass 20 is disposed between the first piezoelectric element 10 and the second piezoelectric element 30. The drive controller 50 is electrically connected with the first piezoelectric element 10 such that the first piezoelectric element 10 will generate a plurality of resonant frequencies, wherein the plurality set of resonant frequencies can be three sets or five sets of resonant frequencies. According to an embodiment of the present invention, the plurality set of resonant frequencies comprises 50.3 kHz, 200.8 kHz, and 408.2 kHz. Since using the drive controller (such as waveform generators, regulators and amplifiers and other circuits) to generate a plurality of staggered resonant frequencies is known in the art, it will not be further described for the sake of brevity. The microprocessor 60 is electrically connected with the first piezoelectric element 10 and uses frequency hopping technology to control sine waves of the plurality set of resonant frequencies to output periodically hopped frequencies, thereby providing an FM (Frequency Modulation) effect.

As shown in FIG. 1A, in the embodiment, the first piezoelectric element 10 and the second piezoelectric element 30 both use the PZT-8 (VP-A80) piezoelectric material. The first piezoelectric element 10 is powered by the power source 100 to generate the oscillation. In other words, in application of the inverse piezoelectric effect, an electric field (voltage) is applied to the first piezoelectric element 10 to elongate the electric dipole moment so that the first piezoelectric element 10 is resistant to the change of electric field and is deformed in the direction of the electric field, thereby generating oscillation. In the first embodiment, the first piezoelectric element 10 is employed as an actuator. Since the oscillation principle of the piezoelectric element is known in the art, it will not be further described for the sake of brevity.

The proof mass 20 transfers the oscillation of the first piezoelectric element 10 to the second piezoelectric element 30 to cause the second piezoelectric element to generate power. In other words, when physical pressure (displacement) generated by the oscillation of the positive piezoelectric effect is applied to the second piezoelectric element, the electric dipole moment of the second piezoelectric element second is reduced by compression, generating equal amounts of positive and negative charges on the surface to maintain the original state and thereby generating electricity, wherein the second piezoelectric element 30 in this embodiment is a power generator. As shown in FIG. 1 A and FIG. 2, in the first embodiment of the piezoelectric system for ultrasonic thermotherapy and electrotherapy 1, the output unit 40 comprises a connecting surface 41 and a tip surface 42, wherein the tip surface 42 is formed in a tapered shape and can be used for non-intrusive acupuncture and single-point electrotherapy for a user 90.

Figure 3:
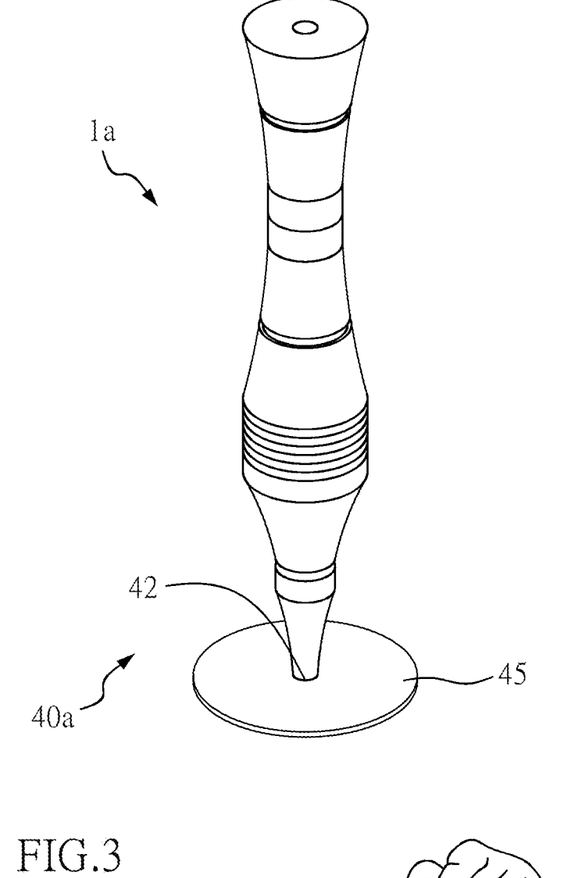
FIG. 3 illustrates a schematic diagram of a second embodiment of the piezoelectric system for ultrasonic thermotherapy and electrotherapy of the present invention.
Figure 4:
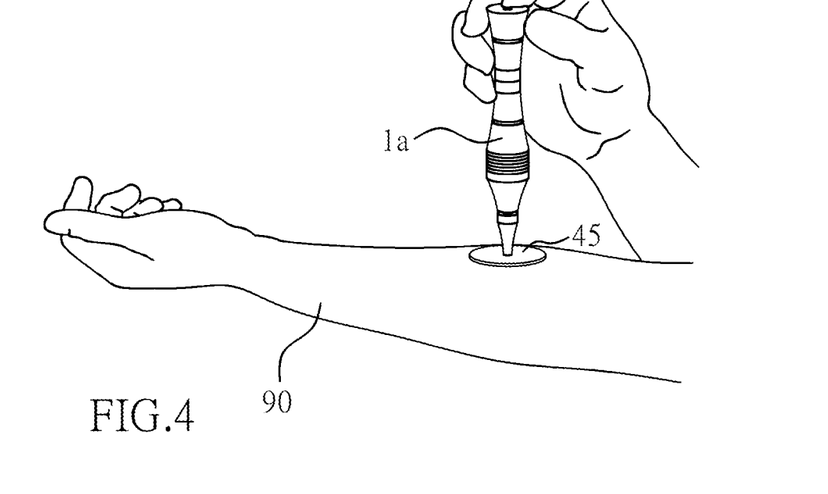
FIG. 4 illustrates an operation diagram of the second embodiment of the piezoelectric system for ultrasonic thermotherapy and electrotherapy of the present invention.

Now please refer to FIG. 3 and FIG. 4 for a schematic diagram and operation diagram of a second embodiment of the piezoelectric system for ultrasonic thermotherapy and electrotherapy of the present invention.

As shown in FIG. 3 and FIG. 4, in the second embodiment of the piezoelectric system for ultrasonic thermotherapy and electrotherapy 1a, the output unit 40a comprises an output surface 45 formed in a disc shape and connected with the tip surface 42. The power and oscillation generated by the piezoelectric system for ultrasonic thermotherapy and electrotherapy 1a are output by the tip surface 42 through the output surface 45, wherein, according to an embodiment of the present invention, the output surface 45 can be applied to facilitate the diffusion of a smeared ointment or gel and increase the absorption of the skin surface of the user 90, and the output surface 45 of the piezoelectric system for thermotherapy and electrotherapy 1a can be only for ultrasound thermotherapy.

Figure 5:
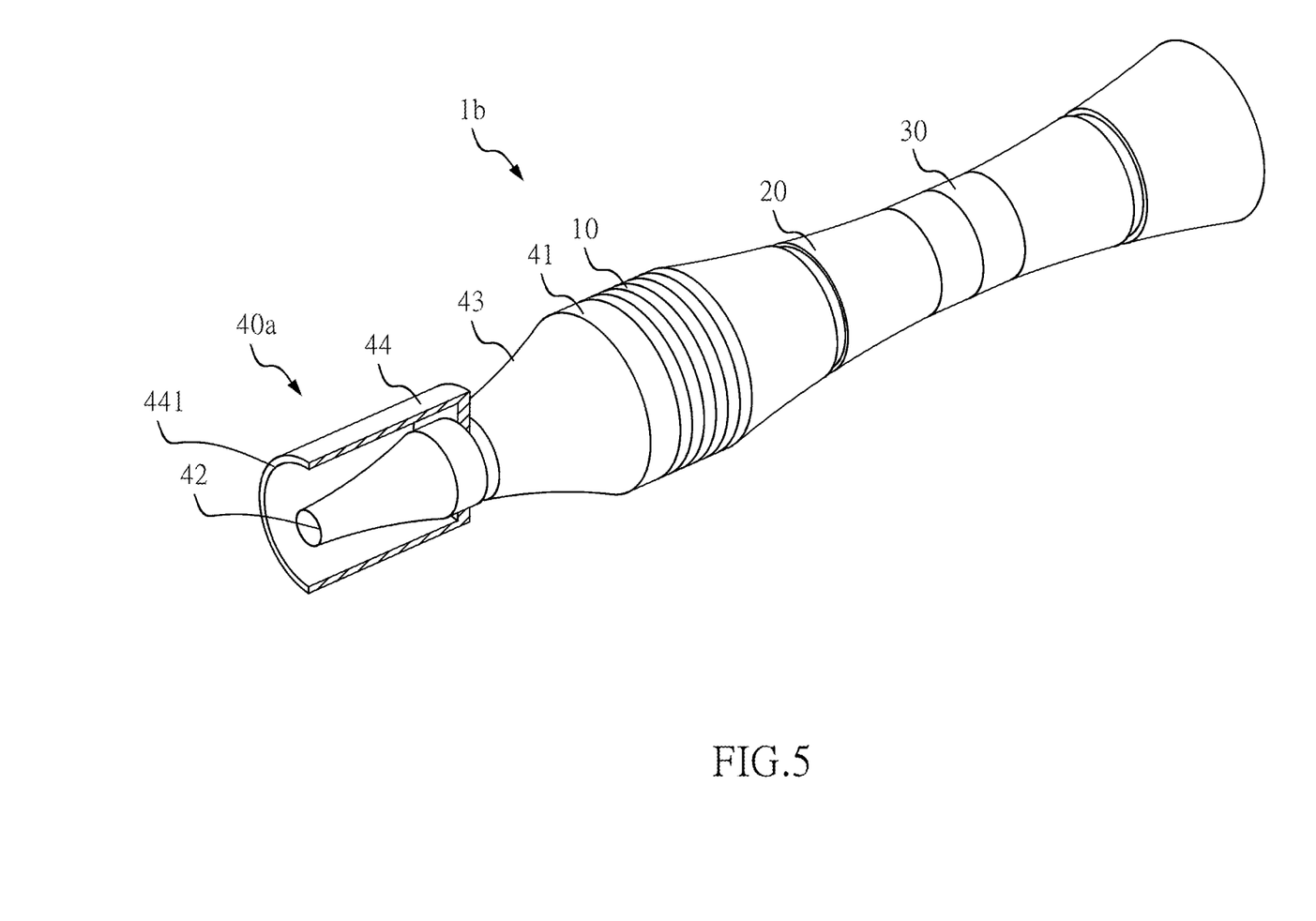
FIG. 5 illustrates a schematic diagram of a third embodiment of the piezoelectric system for ultrasonic thermotherapy and electrotherapy of the present invention.
Figure 6:
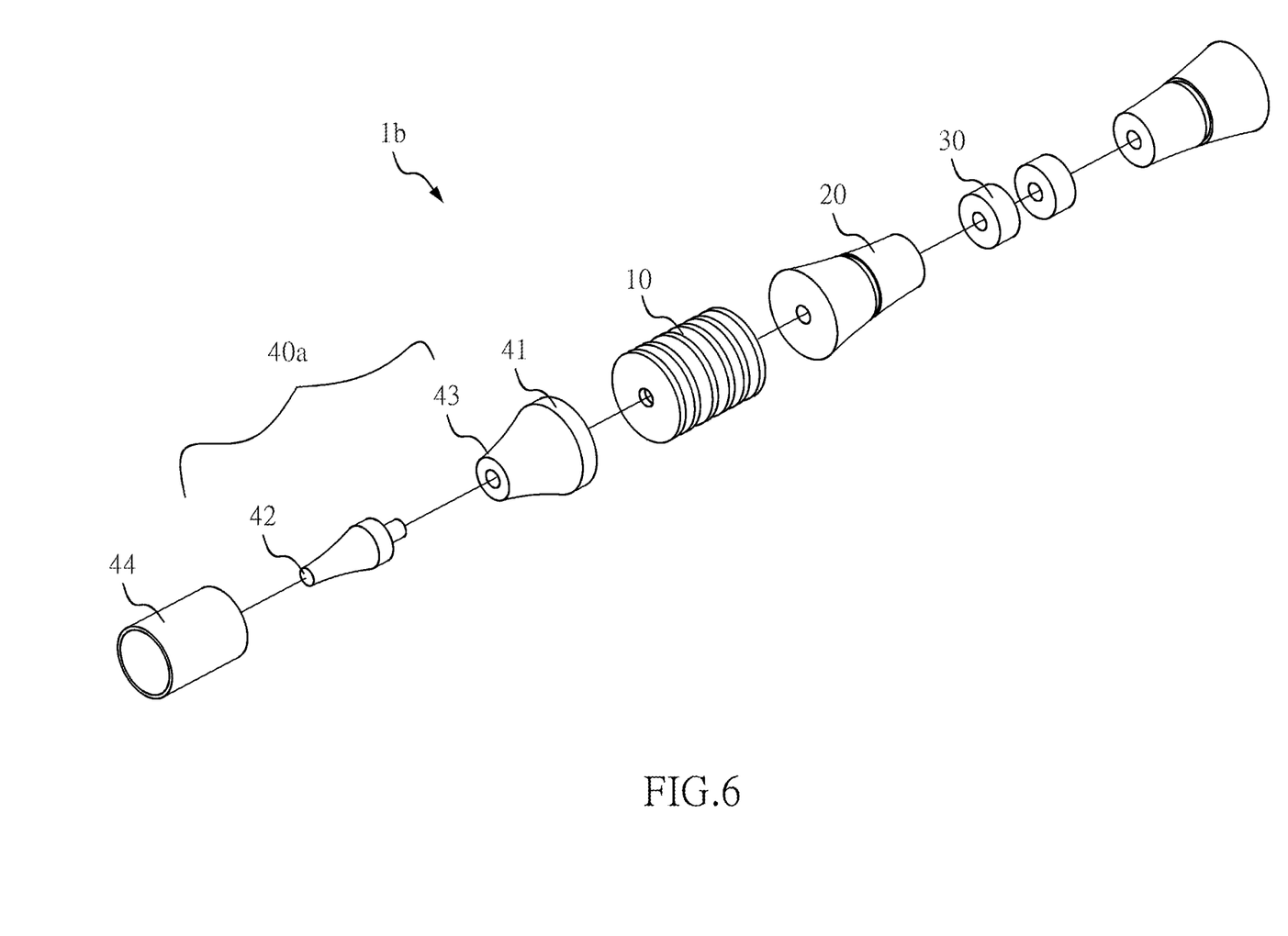
FIG. 6 illustrates an exploded diagram of the third embodiment of the piezoelectric system for ultrasonic thermotherapy and electrotherapy of the present invention.

Now please refer to FIG. 5 and FIG. 6 for a schematic diagram and operation diagram of a third embodiment of the piezoelectric system for ultrasonic thermotherapy and electrotherapy of the present invention As shown in FIG. 5 and FIG. 6, in the third embodiment of the piezoelectric system for ultrasonic thermotherapy and electrotherapy 1b, the output unit 40b comprises a connecting surface 41, a tip surface 42, a tapered output body 43, and a hollow tube body 44. The tapered output body 43 is disposed in the hollow tube body 44. The output unit 40 is electrically connected with the second piezoelectric element 30, wherein the connecting surface 41 is connected with the first piezoelectric element 10 such that the power generated by the second piezoelectric element 30 and the oscillation of the first piezoelectric element 10 are output through the tip surface 42. In this embodiment, the tip surface 42 is the positive output terminal for outputting power; the tip surface 42 provides the effect of electrotherapy, the end surface 441 of the hollow tube body 44 is the negative output terminal, and the end surface 441 outputs high-frequency oscillations that fit the ultrasonic thermotherapy requirements. In the present embodiment, the end surface 441 can be a flat surface, and the end surface 441 enhances the discharge efficiency by surrounding the positive electrode with the negative electrode, thereby enhancing the efficacy by the combined effects of the tip surface 441 and the end surface 441 to achieve the effect of twisting by electrical stimulation and to achieve a hot acupuncture effect by ultrasonic oscillation stimulation at the acupuncture points of the body.

Now please refer to FIG. 7, FIG. 8, FIG. 9A, and FIG. 9B for a schematic diagram, partial diagram of an output unit, a schematic diagram of an end surface of the output unit, and a cross-sectional diagram of the end surface of the output unit of the piezoelectric system for ultrasonic thermotherapy and electrotherapy of the present invention.

Figure 7:
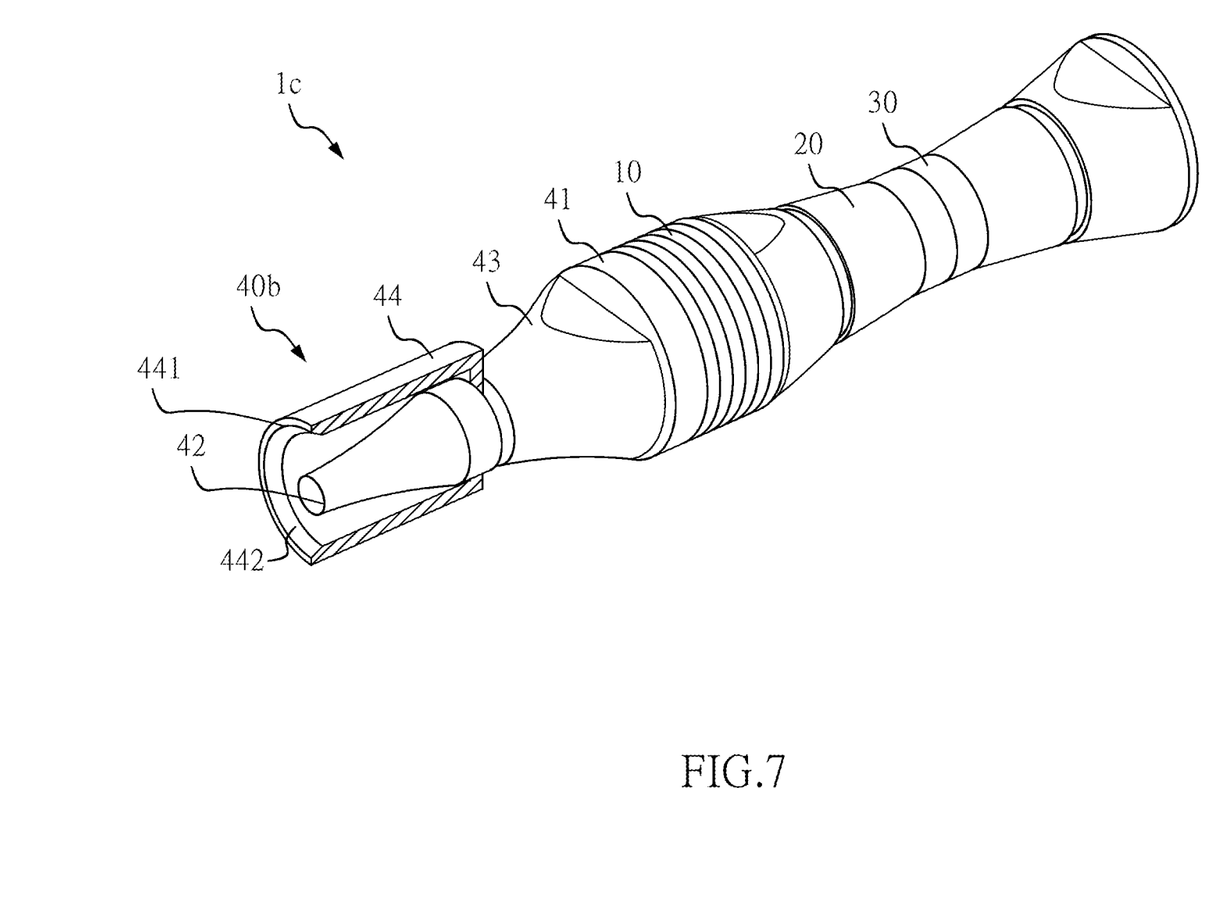
FIG. 7 illustrates a schematic diagram of a fourth embodiment of the piezoelectric system for ultrasonic thermotherapy and electrotherapy of the present invention.
Figure 8:
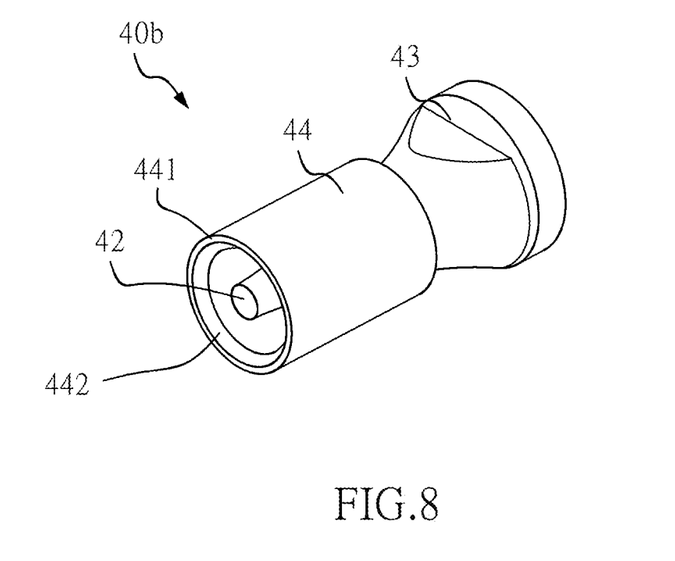
FIG. 8 illustrates a partial diagram of an output unit of the fourth embodiment of the piezoelectric system for ultrasonic thermotherapy and electrotherapy of the present invention.
Figure 9A:
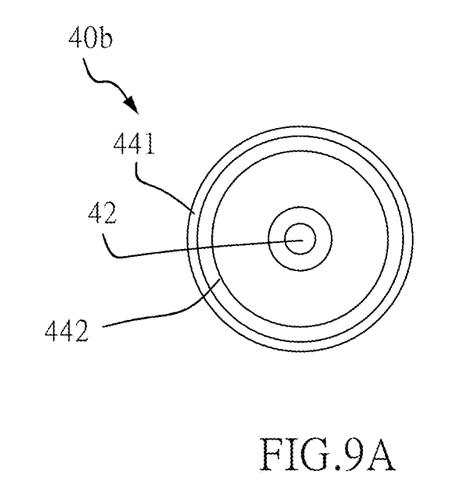
FIG. 9A illustrates a schematic diagram of an end surface of the output unit of the fourth embodiment of the piezoelectric system for ultrasonic thermotherapy and electrotherapy of the present invention.
Figure 9B:
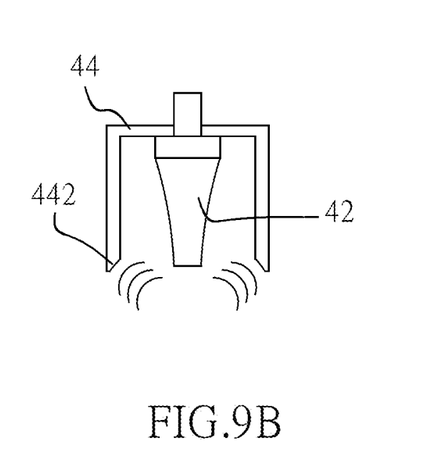
FIG. 9B illustrates a cross-sectional diagram of the end surface of the output unit of the fourth embodiment of the piezoelectric system for ultrasonic thermotherapy and electrotherapy of the present invention.

As shown in FIG. 7 and FIG. 8, in this embodiment, the hollow tube body 44 comprises an end surface 441 and a slant cut surface 442, wherein the slant cut surface 442 is located at the end surface 441 and is used for structural focusing in ultrasonic thermotherapy. As shown in FIGS. 9A and 9B, the end surface 441 of the output unit 40b is negatively charged, and the tip surface 42 of the output unit 40b is positively charged, thereby facilitating electrotherapy by generating an electrical signal loop through the interaction of the positive and negative electrical charges on the surface of the human body, wherein the end surface 441 and the tip surface 42 are in contact with the human body, and the end surface 441 and tip surface 42 output high-frequency oscillations that fit the ultrasonic thermotherapy requirements. In addition, the slant cut surface 442 can guide and concentrate the high-frequency oscillation signals, and can work with the tip surface 42 to enhance the efficacy to achieve the effect of twisting by electrical stimulation and to achieve a hot acupuncture effect by ultrasonic oscillation stimulation at the acupuncture points of the body. It is noted that the tilted angle of the slant cut surface 442 is not limited to any specific angle and can be modified according to actual requirements, as long as it can guide and concentrate the high-frequency oscillation signals to achieve the effect of twisting by electrical stimulation and to achieve a hot acupuncture effect by ultrasonic oscillation stimulation at the acupuncture points of the body.

The present embodiment differs from the third embodiment in that the design of the tip surface 42 and the slant cut surface 442 of the output unit 40b of this embodiment can help concentrate the output of the output unit 40b on the target area to be treated so as to combine the treatments of ultrasonic thermotherapy and electrotherapy and to enhance efficacy. The combined effect of the ultrasonic thermotherapy and electrotherapy of the piezoelectric system for ultrasonic thermotherapy and electrotherapy 1c produces a single-point acupuncture effect; therefore, the piezoelectric system for ultrasonic thermotherapy and electrotherapy 1c can concentrate the ultrasonic waves on the acupuncture points and apply electrical signals to stimulate the acupuncture points to achieve electrical stimulation electrotherapy and to achieve the effect of twisting by electrical stimulation and to achieve a hot acupuncture effect by ultrasonic oscillation stimulation to activate the target area cells.

As mentioned regarding the electro-acupuncture stimulation of the prior art, a bracelet or patch will be worn on the wrist as a negative electrode to form an electrical circuit. Preferably, the present invention provides the piezoelectric system for ultrasonic thermotherapy and electrotherapy 1c, which enhances the single point acupuncture effect by directly surrounding the tip surface 42 (positive electrode) with the end surface 441 (negative electrode). Furthermore, the piezoelectric system for ultrasonic thermotherapy and electrotherapy 1c uses a slant cut surface design to help concentrate the ultrasonic waves on the target area to be treated to achieve a hot acupuncture effect by ultrasonic oscillation stimulation, thereby activating the cells in the target area.

Now please refer to FIG. 1A again. As shown in FIG. 1A, the proof mass 20 comprises a first end surface 21 and a second end surface 22 relative to the first end surface 21, wherein the diameter R1 of the first end surface 21 depends on the diameter of the first piezoelectric element and the diameter R2 of the second end surface 22 depends on the application of the target area to be treated, usually $R_1 > R_2$.

The piezoelectric system for ultrasonic thermotherapy and electrotherapy 1 is used for ultrasonic thermotherapy and electrotherapy; therefore, the suggested ratio between diameter R1 and R2 is $$\frac{R_1}{R_2} = 2,$$

but the present invention is not limited thereto. It is to be noted that the end surface of the first piezoelectric element 10 has a small oscillation amplitude (a few microns), which has to be amplified by horns to enhance the output power. In the embodiment of the piezoelectric ultrasonic system for ultrasonic thermotherapy and electrotherapy 1 of the present invention for ultrasonic thermotherapy and electrotherapy, the proof mass 20 and the output unit 40 are both horns that amplify the oscillations of the end surface of the first piezoelectric element 10; however, since the function of the proof mass 20 differs from that of the output unit output unit 40, the proof mass 20 and the output unit 40 have different design restrictions respectively.

As shown in FIG. 1 A, in the present embodiment, the proof mass 20 acting as one of the horns comprises a first length L1, and the first length first length L1 is obtained by the following formula:

$$L_1 = \frac{c}{2f}\left[1 + \left(\frac{\ln N}{\pi}\right)^2\right]^{\frac{1}{2}},$$

where c is a longitudinal acoustic velocity and f is an operating frequency of the piezoelectric system for ultrasonic thermotherapy and electrotherapy 1. According to a preferred embodiment of the present invention, the operating frequency of the piezoelectric system for ultrasonic thermotherapy and electrotherapy 1 can be the average value of the plurality of resonant frequencies generated by the first piezoelectric element 10. In a preferred embodiment of the present invention, c=6300 m/s, $R_1$=30 mm, $R_2$=15 mm, f=150 kHz, $$N = \frac{R_1}{R_2} = 2;$$

therefore, the first length L1 is 21.5 mm, as determined by inserting the above-mentioned parameters into the formula.

Since the output unit 40 is also a horn for amplifying the oscillation of the end surface of the first piezoelectric element 10, restrictions apply to the sizes of the connecting surface 41, the tip surface 42, and the output unit 40, wherein the diameter R3 of the connecting surface 41 depends on the diameter of the first piezoelectric element 10 and the diameter R4 of the tip surface 42 depends on the application of the target area to be treated. According to an embodiment of the present invention, the piezoelectric systems for ultrasonic thermotherapy and electrotherapy 1, 1a, 1b are provided for ultrasonic thermotherapy and electrotherapy; therefore, the ratio between the diameter R3 and R4 can be $$\frac{R_3}{R_4} = 10,$$

but the present invention is not limited thereto. Further, the output unit 40 comprises a second length L2, which can be obtained by the following formula:

$$L_2 = \frac{c}{2f}\left[1+\left(\frac{\ln N}{\pi}\right)^2\right]^{\frac{1}{2}},$$

where c is a longitudinal acoustic velocity and f is an operating frequency of the piezoelectric system for ultrasonic thermotherapy and electrotherapy. According to a preferred embodiment of the present invention, the operating frequency of the piezoelectric systems for ultrasonic thermotherapy and electrotherapy 1, 1a, 1b can be the average value of the plurality of resonant frequencies generated by the first piezoelectric element 10. In a preferred embodiment of the present invention, c=6300 m/s, $R_1$=30 mm, $R_2$=3 mm, f=150 kHz, $$N = \frac{R_3}{R_4} = 10;$$

therefore, the second length L2 is 26 mm, determined by inserting the above-mentioned parameters into the formula.

Now please refer to FIG. 10, FIG. 11, FIG. 12A, and FIG. 12B for a schematic diagram, a partial diagram of the output unit, a schematic diagram of an end surface of the output unit, and a cross-sectional diagram of the end surface of the output unit of a fifth embodiment of the piezoelectric system for ultrasonic thermotherapy and electrotherapy of the present invention.

Figure 10:
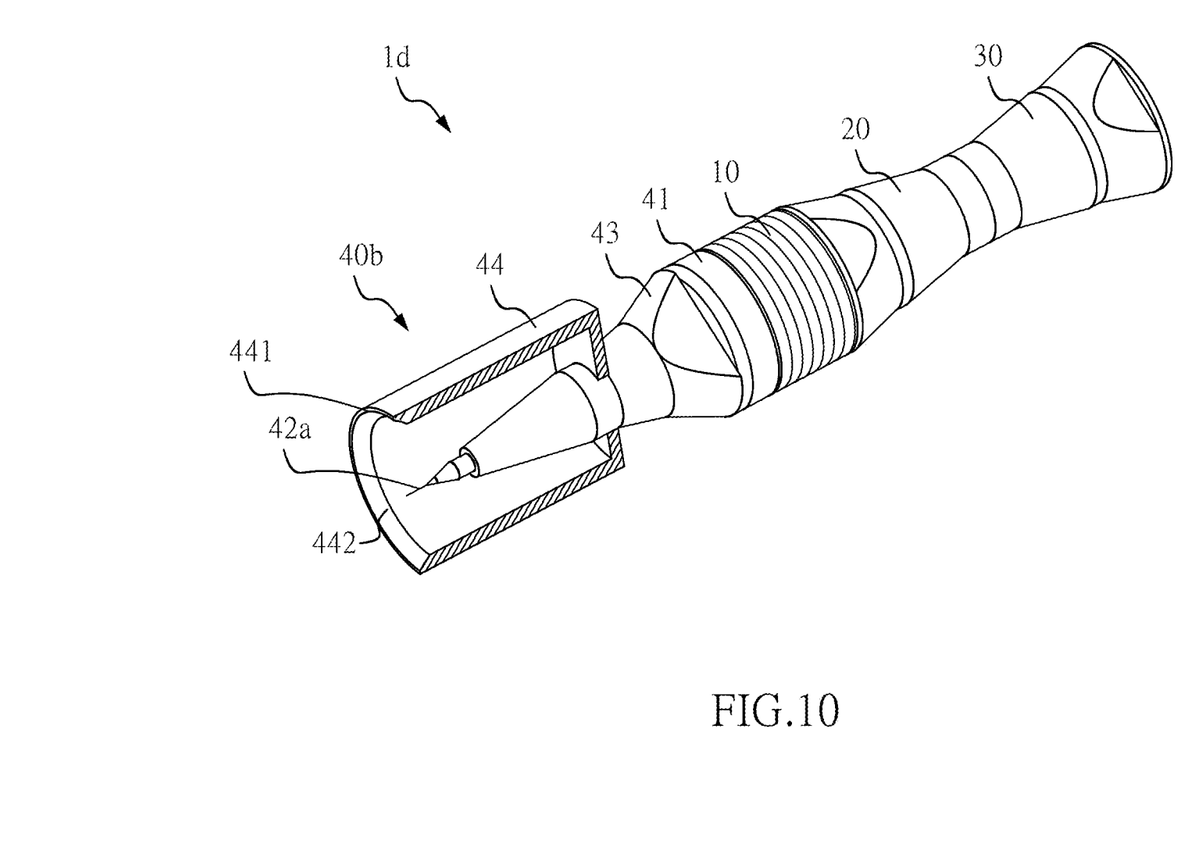
FIG. 10 illustrates a schematic diagram of a fifth embodiment of the piezoelectric system for ultrasonic thermotherapy and electrotherapy of the present invention.
Figure 11:
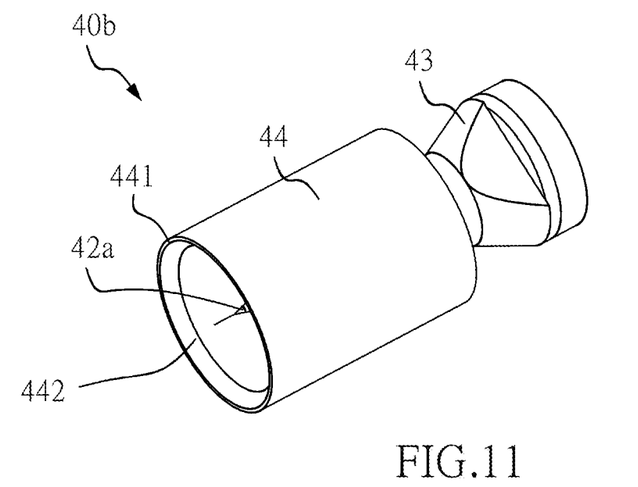
FIG. 11 illustrates a partial diagram of an output unit of the fifth embodiment of the piezoelectric system for ultrasonic thermotherapy and electrotherapy of the present invention.

As shown in FIGS. 10 and 11, in the present embodiment, the output unit 40b has a tapered tip surface 42a shaped like a needle, and the remaining details are the same as those of the first embodiment; the hollow tube body 44 comprises an end surface 441 and a slant cut surface 442, wherein the slant cut surface 442 is located at the end surface 441 and is used for structural focusing in ultrasonic thermotherapy. As shown in FIGS. 9A and 9B, the end surface 441 of the output unit 40b is negatively charged, and the tip surface 42 of the output unit 40b is positively charged, thereby facilitating electrotherapy by generating an electrical signal loop with the interaction of the positive and negative electrical charges on the surface of the human body, wherein the end surface 441 and the tip surface 42 are in contact with the human body, and the end surface 441 and tip surface 42 output high-frequency oscillations that fit the ultrasonic thermotherapy requirements. In addition, the slant cut surface 442 can guide and concentrate the high-frequency oscillation signals and work with the tip surface 42 to enhance the efficacy to achieve the effect of twisting by electrical stimulation and to achieve a hot acupuncture effect by ultrasonic oscillation stimulation at the acupuncture points of the body. It is noted that the tilted angle of the slant cut surface 442 is not limited to any specific angle and can be modified according to actual requirements, as long as it can guide and concentrate the high-frequency oscillation signals to achieve the effect of twisting by electrical stimulation and to achieve a hot acupuncture effect by ultrasonic oscillation stimulation at the acupuncture points of the body.

Figure 12A:
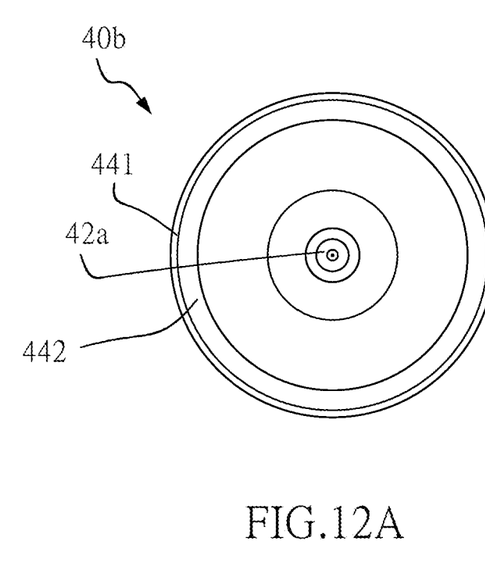
FIG. 12A illustrates a schematic diagram of an end surface of the output unit of the fifth embodiment of the piezoelectric system for ultrasonic thermotherapy and electrotherapy of the present invention.
Figure 12B:
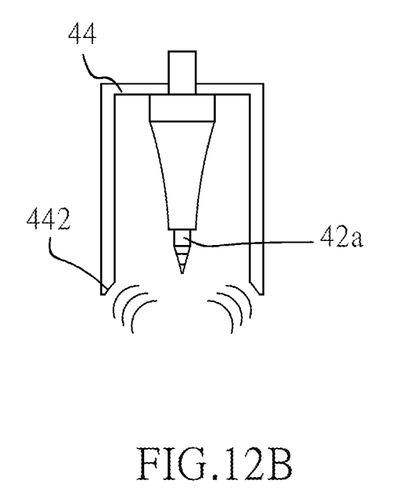
FIG. 12B illustrates a cross-sectional diagram of the end surface of the output unit of the fifth embodiment of the piezoelectric system for ultrasonic thermotherapy and electrotherapy of the present invention.

The tip surface 42 is designed to allow structural focusing for ultrasonic thermotherapy, as shown in FIG. 12B. The area near the tip surface 42a is the interaction area of the positive electrode (tip surface 42a) and the ring-shaped negative electrode (end surface 441), where the electrical stimulation of the waveform signal for shallow electrotherapy is input thereto; the end surface 441 and the tip surface 42a are in contact with the human body and are provided for outputting high-frequency oscillations that fit the ultrasonic thermotherapy requirements. Further, the slant cut surface 442 can guide and concentrate the high-frequency oscillation signals and work with the electrotherapy area of the tip surface 42 to enhance the efficacy to achieve the effect of twisting by electrical stimulation and to achieve a hot acupuncture effect by ultrasonic oscillation stimulation at the acupuncture points of the body.

Figure 13:
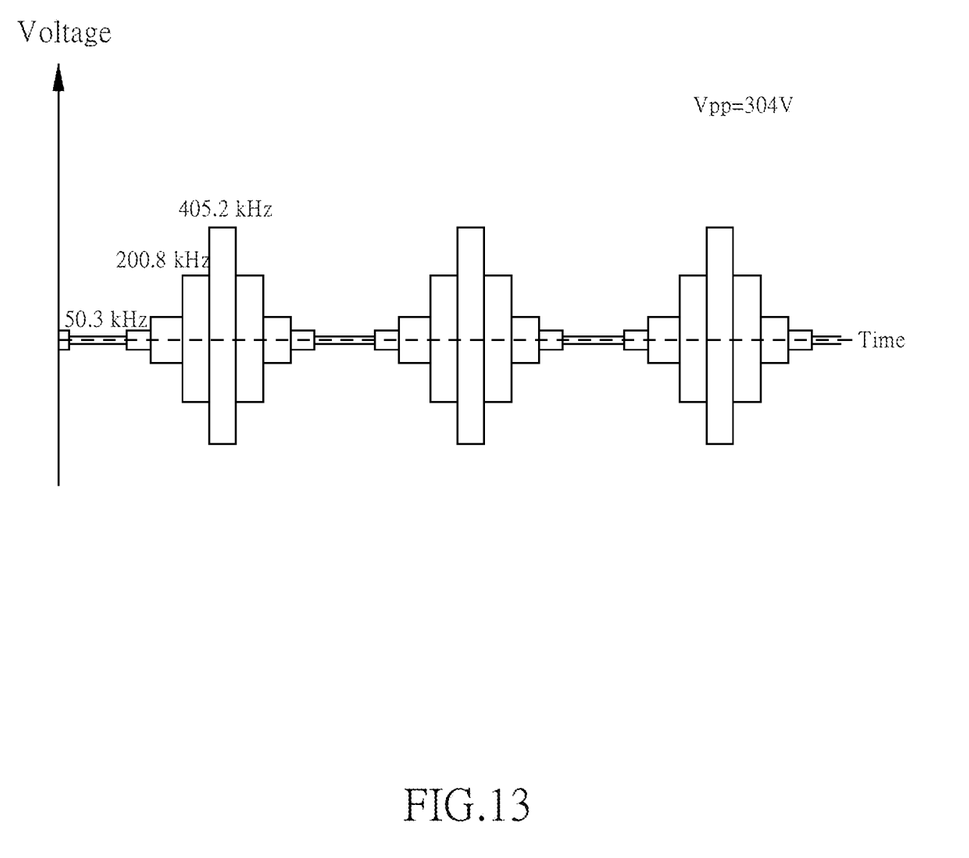
FIG. 13 illustrates a simulated and converted amplitude modulation wave diagram of three sets of resonant frequencies of the piezoelectric system for ultrasonic thermotherapy and electrotherapy using frequency hopping control.

Please refer to both FIG. 1B and FIG. 13, the latter of which illustrates a simulated and converted amplitude modulation wave diagram of three sets of resonant frequencies of the piezoelectric system for ultrasonic thermotherapy and electrotherapy using frequency hopping control.

As shown in FIG. 1B, the first piezoelectric element 10 is powered by the power source 100 to generate oscillation and is controlled by the drive controller 50 to generate a plurality of resonant frequencies. According to experimental results, three resonant frequency points 50.3 kHz, 200.8 kHz and 408.2 kHz can be obtained, and square waves of these three frequencies 50.3 kHz, 200.8 kHz and 408.2 kHz are output by a microprocessor 60, wherein an energy-converted and simulated AM (amplitude modulation) waveform is obtained, and the resultant effect is shown in FIG. 13. The first piezoelectric element 10 is controlled by the microprocessor 60 to output oscillations having the amplitude modulation waveform, and the first piezoelectric element 10 and the second piezoelectric element 20 can be switched among different modes, in which voltages of the different amplitudes are output and combined to simulate the best full amplitude modulation waveform. At the same time, the piezoelectric system for ultrasonic thermotherapy and electrotherapy 1 of this embodiment is designed with reference to electrotherapy specifications so as to meet the frequency and voltage standards for ultrasonic thermotherapy and electrotherapy.

It is noted that there are two ways to control the second piezoelectric element 20 to generate an ideal amplitude modulation waveform. One way is to control the voltage of the power source 100 inputted to the first piezoelectric element 10. It can be seen from the inverse piezoelectric effect that when a larger voltage is inputted, the first piezoelectric element 10 may generate a linearly positive correlated displacement output, and when the displacement output increases, the force applied on the second piezoelectric element 20 also increases and thus causes changes in the power output. The second way is to find the resonant frequency of the piezoelectric ultrasonic thermotherapy and electrotherapy 1 to be switched. In the case of fixed input voltage, different resonant frequencies will generate different displacement outputs; however, the change of the displacement output is not linear, causing the second piezoelectric element 30 to change the power output as well. When the human body receives a fixed frequency signal, its cells will adapt to the signal and fail to respond to the voltage change; therefore, the piezoelectric system for ultrasonic thermotherapy and electrotherapy 1 must change its frequencies. In one embodiment of the invention, the piezoelectric system for ultrasonic thermotherapy and electrotherapy 1 employs the second way.

As described above, since the first piezoelectric element 10 and the second piezoelectric element 30 are different in size, their resonant frequencies are different as well, so when the piezoelectric system for ultrasonic thermotherapy and electrotherapy 1 operates, the following three cases may occur: 1. the first piezoelectric element resonates but the second piezoelectric element does not, so the second piezoelectric element 30 experiences large applied force but generates low efficiency power output; 2. the first piezoelectric element 10 does not resonate but the second piezoelectric element 30 does, so the second piezoelectric element 30 experiences smaller applied force but generates higher efficiency power output; 3. the first piezoelectric element 10 and the second piezoelectric element 30 both resonate, and the second piezoelectric element 30 has a large displacement and generates high efficiency power output.

During actual operation, the piezoelectric system for ultrasonic thermotherapy and electrotherapy 1 of the present invention does not need to operate in the third case because the amplitude modulation waveform can be modulated with some relatively low voltage output. The third case occurs at the peak of the amplitude modulation, while the first and second cases can be mixed to generate a desired waveform. It is not necessary for the microprocessor 60 to synthesize only three frequencies, since the human body adapts well to progressive signals; the microprocessor can use more than five frequencies to synthesize the output. In addition, the general electrotherapy instrument can provide amplitude modulation waveform output; therefore, the drive controller 50 can include pulse signals with intermittent changes in the design. Further, by using frequency control, the piezoelectric system for ultrasonic thermotherapy and electrotherapy 1 can achieve resonant frequencies of up to 750 kHz to meet the resonant frequency regulations of ultrasonic thermotherapy.

The piezoelectric systems for ultrasonic thermotherapy and electrotherapy 1, 1a, 1c, 1d of the present invention comprise two piezoelectric elements, wherein the first piezoelectric element 10 is used as an actuator and is driven by the power source to generate a high amplitude oscillation, which is partly transferred by the proof mass 20 to the second piezoelectric element 30, and the second piezoelectric element 30 receives part of the oscillation energy from the first piezoelectric element 10 and generates power for medical applications based on the piezoelectric effect, thereby providing the voltage required for physical electrotherapy and the oscillation for ultrasonic therapy at the tip surface 42.

The piezoelectric systems for ultrasonic thermotherapy and electrotherapy 1, 1a, 1c, 1d are different from the traditional electro-acupuncture instrument. Most traditional electronic needles use wrist bracelets to provide electrical circuit conduction, or they require users to sit in chairs containing negative electrodes to help form electrical stimulation circuit loops. The end surface 41 and the tip surfaces 42, 42a, 42c of the piezoelectric systems for ultrasonic thermotherapy and electrotherapy 1, 1a, 1c, 1d jointly provide a single-point stimulation effect to small areas. The output end face 41 (negative electrode) and the tip surfaces 42, 42a, 42c (positive electrode) of the piezoelectric systems for ultrasonic thermotherapy and electrotherapy 1, 1a, 1c, 1d can provide electrical stimulation interaction on the target area to be treated and also introduce the use of an ultrasonic thermotherapy mechanism; therefore, the piezoelectric systems for ultrasonic thermotherapy and electrotherapy 1, 1a, 1c, 1d not only can stimulate the target cells and enhance drug absorption efficiency but also provide both electrical stimulation and ultrasonic thermotherapy. Therefore, the piezoelectric systems for ultrasonic thermotherapy and electrotherapy 1, 1a, 1c, 1d of the present invention combine the best of both ultrasonic thermotherapy and electrotherapy to improve efficacy.

It is noted that the above-mentioned embodiments are only for illustration. It is intended that the present invention cover modifications and variations of this invention provided they fall within the scope of the following claims and their equivalents. Therefore, it will be apparent to those skilled in the art that various modifications and variations can be made to the structure of the present invention without departing from the scope or spirit of the invention.

What is claimed is:

1. A piezoelectric system for ultrasonic thermotherapy and electrotherapy applied on a working surface, comprising:
    a first piezoelectric element powered by a power source to generate an oscillation;
    a second piezoelectric element;
    a proof mass disposed between the first piezoelectric element and the second piezoelectric element, the proof mass being provided for transferring the oscillation to the second piezoelectric element so as to cause the second piezoelectric element to generate power; and
    an output unit comprising a connecting surface, a hollow tube body and a tip surface, the first piezoelectric element being disposed between the output unit and the proof mass, the output unit being electrically connected with the second piezoelectric element, the tip surface being disposed within a hollow portion of the hollow tube body,
    wherein the connecting surface is connected with the first piezoelectric element and the tip surface is formed in a tapered shape such that the oscillation from the first piezoelectric element and the electrical power generated by the second piezoelectric element are output through the tip surface, and
    wherein the tip surface is a positive output terminal of the power source and an end surface of the hollow tube body is a negative output terminal of the power source and both the tip surface and the end surface are adapted to touch the working surface.

2. The piezoelectric system for ultrasonic thermotherapy and electrotherapy as claimed in claim 1, wherein the hollow tube body comprises a slant cut surface located at the end surface.

3. The piezoelectric system for ultrasonic thermotherapy and electrotherapy as claimed in claim 1, comprising a drive controller electrically connected with the first piezoelectric element to drive the first piezoelectric element at a plurality of resonant frequencies.

4. The piezoelectric system for ultrasonic thermotherapy and electrotherapy as claimed in claim 3, wherein the plurality of resonant frequencies is the resonant frequencies of the first piezoelectric element and the second piezoelectric element coupling with each other.

5. The piezoelectric system for ultrasonic thermotherapy and electrotherapy as claimed in claim 3, comprising a microprocessor electrically connected with the first piezoelectric element, wherein the microprocessor uses frequency hopping technology to control square waves of the plurality set of resonant frequencies to output periodically hopped frequencies, thereby providing a Frequency Modulation (FM) effect.

6. The piezoelectric system for ultrasonic thermotherapy and electrotherapy as claimed in claim 1, wherein the proof mass comprises a first end surface and a second end surface relative to the first end surface, the first end surface comprises a diameter R1, the second end surface comprises a diameter R2, and the proof mass comprises a first length L1, which is obtained by the following formula:

$$L_1 = \frac{c}{2f}\left[1+\left(\frac{\ln N}{\pi}\right)^2\right]^{\frac{1}{2}},$$

where c is a longitudinal acoustic velocity, f is an operating frequency of the piezoelectric system for ultrasonic thermotherapy and electrotherapy, and $$N = \frac{R_1}{R_2},$$

where N is a diameter ratio of the first end surface to the second end surface.

7. The piezoelectric system for ultrasonic thermotherapy and electrotherapy as claimed in claim 6, wherein the connecting surface comprises a diameter R3, the tip surface comprises a diameter R4, and the output unit comprises a second length L2, wherein the second length L2 is obtained by the following formula:

$$L_2 = \frac{c}{2f}\left[1+\left(\frac{\ln N}{\pi}\right)^2\right]^{\frac{1}{2}},$$

where c is a longitudinal acoustic velocity, f is the operating frequency of the piezoelectric system for ultrasonic thermotherapy and electrotherapy, and $$N = \frac{R_3}{R_4},$$

where N is a diameter ratio of the connecting surface to the tip surface.

8. The piezoelectric system for ultrasonic thermotherapy and electrotherapy as claimed in claim 1, wherein the connecting surface comprises a diameter R3, the tip surface comprises a diameter R4, and the output unit comprises a second length L2, wherein the second length L2 is obtained by the following formula:

$$L_2 = \frac{c}{2f}\left[1+\left(\frac{\ln N}{\pi}\right)^2\right]^{\frac{1}{2}},$$

where c is a longitudinal acoustic velocity, f is the operating frequency of the piezoelectric system for ultrasonic thermotherapy and electrotherapy, and $$N = \frac{R_3}{R_4},$$

where N is a diameter ratio of the connecting surface to the tip surface.

\* \* \* \* \*